United States Patent [19]

Reiff

[11] Patent Number: 4,475,556

[45] Date of Patent: Oct. 9, 1984

[54] RAPID MEASUREMENT OF COLLOID OSMOTIC EQUILIBRIUM PRESSURE

[76] Inventor: Theodore R. Reiff, Apt. C-301, 77 Pond Ave., Brookline, Mass. 02146

[21] Appl. No.: 454,984

[22] Filed: Jan. 3, 1983

[51] Int. Cl.³ .......................... A61B 5/02; G01N 7/10
[52] U.S. Cl. ...................................... 128/673; 73/64.3
[58] Field of Search ............... 128/630, 632, 637, 668, 128/672, 673; 73/64.3

[56] References Cited

U.S. PATENT DOCUMENTS

| | | | |
|---|---|---|---|
| 3,063,288 | 11/1962 | Reiff | 73/64.3 |
| 3,572,315 | 3/1971 | Cullen | 128/632 |
| 3,952,730 | 4/1976 | Key | 128/632 |
| 4,245,495 | 1/1981 | Kakiuchi et al. | 73/64.3 |

OTHER PUBLICATIONS

"An Intravascular Protein Osmometer", Hensen, J. W. and Brace, R. A., American Physiological Society, 1983.

Advertisement, Millar Instrument Co., Houston, Texas.

Primary Examiner—Gerald Goldberg
Assistant Examiner—Hezron E. Williams
Attorney, Agent, or Firm—Hamilton, Brook, Smith & Reynolds

[57] ABSTRACT

Rapid colloidal osmometer 10 for readout of osmotic equilibrium pressure comprising a cap of rigid semipermeable ceramic 12, a solvent chamber 14 and a pressure transducer 18. The osmometer is for insertion into a living subject. Osmotic equilibrium pressure is calculated by a data reduction computer 40 and displayed on a chart recorder 42. The computer can also be used to control fluid infusion through a valve 44 into a patient 29. An alternate embodiment comprises an osmometer for high pressure use in a pressure chamber 54 in which the osmometer 56 is braced 58. A solution chamber 57, semipermeable membrane 32, and solvent 55 are held at a high pressure by compressor 78. Osmotic equilibrium is predicted by a computer 40 and displayed on a chart recorder 42.

11 Claims, 9 Drawing Figures

RAPID MEASUREMENT OF COLLOID OSMOTIC EQUILIBRIUM PRESSURE

DESCRIPTION

This invention relates in general to osmometers and methods of measuring osmotic pressure, reference being had in particular to the measurement of colloid osmotic pressure in vivo, in concentrated solutions of substances with relatively high molecular weights and/or in instances subjected to high external pressure.

BACKGROUND OF THE INVENTION

When two solutions having different concentrations of a dissolved substance, or solute, are separated from each other by a semi-permeable membrane, permeable only to a solvent, it is found that solvent passes from the less concentrated solution to the more concentrated solution more rapidly than from the more concentrated to the less concentrated solution. This tends to equalize the concentrations of the dissolved substance in the two solutions. This process is called osmosis.

Figure 1:
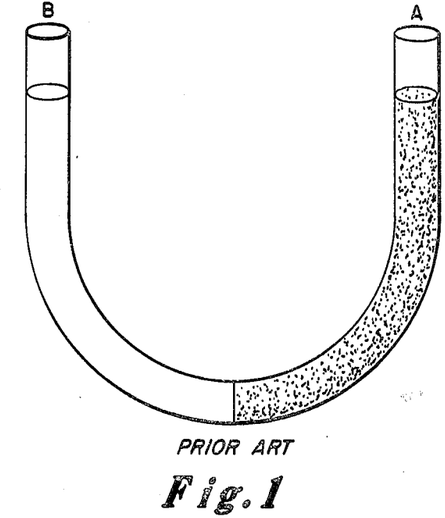
FIG. 1 is a plan view of a prior art U-tube divided by a semipermeable membrane.

Laboratory measurement of osmosis is often done with a U-tube or similar device as shown in FIG. 1. The U-tube is divided at its base by a semi-permeable membrane. Supposing now that Side A contains a solution in which the solute sugar is dissolved in the solvent water. Side B contains an equal quantity of pure water and both sides are subject to the same initial temperature and pressure. If the membrane is permeable to water and not to sugar, water molecules will be able to pass in both directions from A to B and B to A.

Water molecules will traverse the membrane from B to A much more often than from A to B because water will tend to move from a solution with fewer dissolved particles per unit volume to a solution with more dissolved particles per unit volume. This is because the chemical potential (free energy per mole) of a solvent is decreased if other substances are dissolved in it. The decrease of free energy of the solvent varies directly with the number of dissolved particles per unit volume.

Figure 2:
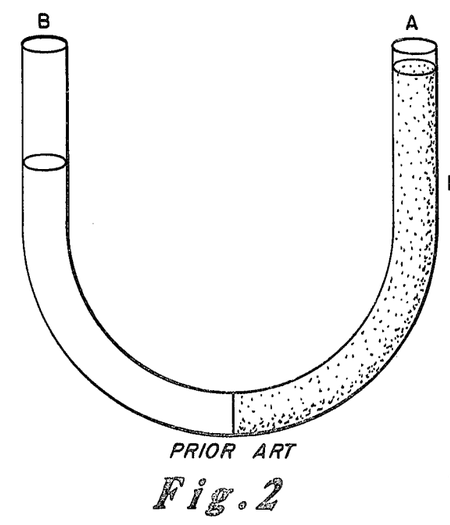
FIG. 2 is a plan view of the U-tube of FIG. 1 showing the results of osmosis.

FIG. 2 shows that as a net result, column A becomes higher than column B. An equilibrium is reached when the increased pressure of column A exerted on the solution is great enough for water molecules to be forced to cross the membrane from A to B as fast as they move into A from B. When this point is reached, water is passing through the membrane in opposite directions at the same rate and the system is in equilibrium. In this case, the osmotic equilibrium pressure upon the solution is produced by gravity, but this is not necessarily the case.

In a closed system where two volumes are held in closed containers, the increase in volume of liquid on one side of the membrane nd the decrease in the other will result in a net pressure differential equivalent to the hydrostatic gravitational pressure of the above example. Osmotic pressure is therefore defined as the algebraic sum of that positive and negative pressure which must be exerted on the solution and the solvent respectively in order to keep solvent transfer from the solution in equilibrium with solvent transfer from pure solvent when the two volumes are separated by a semi-permeable membrane.

Any solution or colloid fluid can be described as having a characteristic potential osmotic pressure. Osmotic pressure of a solution of colloid is therefore a measure of the tendency of solvent to move into it by osmosis. Osmotic pressure of colloids is also known as oncotic pressure.

Osmometers presently known in the art are subject to a number of limitations which detract materially from their medical usefulness and the efficiency of measuring oncotic pressures. For example, osmotic studies of biological fluids by conventional methods require relatively large liquid volumes or disposable samples and excessive amounts of time.

There is also the need for maintaining precise temperature control and proper semi-permeable membrane characteristics during the time it takes to record osmotic pressure. Conventional osmometers have not been able to take a measurement in a short enough time so as to be consistently usable either in an in vivo environment or when osmotic pressures are very high.

I have previously disclosed in my U.S. Pat. No. 3,063,288 a method and apparatus for measuring colloid osmotic pressures. While this apparatus has been useful in measuring the osmotic pressure of small amounts of solutions, it is not amenable to the purpose of this invention. I have revised and improved upon the principles of that invention to allow for osmotic readings to be made in vivo and in highly concentrated solutions in a much shorter amount of time.

Because of their shortcomings, conventional osmometers have not been useful in many medical areas in which water balance is a primary concern. Water balance is particularly of concern in the study of aging. It has been determined that the percentage of water in the human body decreases as a person ages. For example, an embryo is 90% water, a fetus and newborn child is 80%, a mature adult 70%, and an older adult may have percentages of body water in the 60's or even 50's. It is suspected that there is some profound relationship between water and aging. A way of measuring the loss of water in cells in the body is by measuring osmotic pressure. The physical phenomenon controlling water in cells is the oncotic pressure (colloid osmotic pressure) due to the presence of macromolecules, large protein molecules, within the cell. It is through study of this osmotic relationship in the cell that one might be able to understand some of the changes that occur with aging.

An improved osmometer would also be useful in the study of sickle-cell anemia. Sickle-cell anemia is a disease in which the hemoglobin in red blood cells, when exposed to low partial pressures of oxygen, contracts into an aggregate called a tactoid. The tactoid appears to occur when the cell water diffuses out of the cell due to solute-solute interaction of aggregating hemoglobin, a macromolecule. The aggregation of the hemoglobin molecules disrupts the osmotic equilibrium within the cell to the point where the solvent (water) cannot be retained within the sickle cell. The dehydrated cell then becomes sickled and is unable to operate effectively in transporting oxygen in the body. If a way could be found to reduce the solute-solute interaction, and the subsequent water loss, the sickling phenomena might be interrupted.

Control of intravascular blood volume through osmotic pressure is an important element in kidney dialysis and intravenous saline infusion. The rate of infusion of fluid into a patient in either of these situations must be carefully controlled. If the saline or dialysis increases the volume of fluid solvent in the patient beyond the normal limits, patients may suffer from hypervolemia which can produce congestive heart failure or pulmonary edema. Conversely, too little fluid solvent in the system may result in hypovolemia which produces hypotension and shock. It is therefore reasonable to expect that constant on-line measurement of intravascular colloid osmotic pressure would be useful for controlling either kidney dialysis or intravenous saline infusions as currently practiced in the medical world.

Another use for osmotic measurement for regulated control of body fluids is in space flight. Currently the only people going to and from the space environment are American and Soviet astronauts in top physical form. In the near future less physically trained personnel will be undergoing the transition to and from the space environment. When a person travels into space, the gravitational field changes and approaches zero; therefore, the gravitational pressure or hydrostatic pressure head of the cardiovascular system also goes to zero. This hydrostatic pressure head is important in maintaining osmotic equilibrium in the body. Transport of water into the vascular system rises with this physiological change and can result in an overload of the circulatory system as in the previously described hypervolemia. On initial exposure to the space environment, an astronaut's vascular system may be excessively stressed from the rise in intravascular volume due to transport of solvent into the vascular system. This might result in a fatal cardiovascular load for some personnel. The converse results in a return from zero gravity to earth. On returning to earth, astronauts have fainted in part due to decreases in plasma volume. This has been particularly true in long duration space flight. Currently the United States, European nations and the Soviet Union have plans to launch manned space stations. The personnel sent to these space stations will live there for long durations which will make them more susceptible to hypovolemia on their return. It is therefore important to mitigate these osmotic stresses on voyages to and from space.

A mitigation of space related colloid osmotic problems would allow for the transport of sick and injured patients into the space environment. Through in vivo colloid osmotic controls, a space hospital might be able to safely receive patients burned over large parts of their bodies, or paralyzed patients. Such patients, freed from gravitational stresses, might be able to function more adequately and be treated more effectively. Burn and paralyzed patients would not have to be turned to avoid pressure sores, and paralyzed patients, freed from the force of gravity might, with the minimal amount of strength they have remaining, be able to function more effectively. Through control of intravascular colloid osmotic pressure, patients would be able to get into space without being subject to mortal stresses upon route. Furthermore, the same sort of colloid osmotic control may be necessary on return to earth from long duration space missions.

DISCLOSURE OF THE INVENTION

In accordance with principles of this invention, a rapid colloid osmometer for rapid readout of osmotic equilibrium is possible. The device is shaped as a small pen-like rod or capsule having a semipermeable cap covering a solvent chamber adjacent to a first pressure transducer (providing a first pressure output). Osmotic pressure is read from the first pressure transducer when the device is inserted into a living subject. Osmosis occurs across the semipermeable cap.

A second pressure transducer may be mounted within the capsule to directly measure the hydrostatic pressure of the fluid in which the capsule is implanted. The capsule diameter is preferably between one and two millimeters in diameter.

The signal from the first pressure transducer minus the ambient pressure recorded from the second transducer is processed by a computer which is programmed to calculate the rate of change across the semipermeable membrane and project the osmotic equilibrium pressure. The results of the computer calculations and the pressures read by the transducers are recorded on a chart recorder or other similar electronic recording devices.

In a preferred embodiment the computer may also be programmed to control through a valve the rate of fluid infusion into a living subject. This controls that subject's intravascular colloid osmotic pressure which, in the absence of loss of blood or colloid, bears an explicit inverse relationship to plasma volume.

In an alternative embodiment of the invention, for measurement of ultra high colloid osmotic pressure, an osmometer is mounted inside a pressure chamber. The osmometer is placed within a pressure chamber whose pressure is controlled by an external compressor and pressure gauge.

The osmometer is comprised of a solvent chamber, semipermeable membrane and a test solution chamber. The solution is a test solution for which osmotic equilibrium is to be determined. A signal is transmitted from a pressure transducer in the osmometer to a computing device. The computing device computes the rate of change of osmotic pressure in the sealed solvent chamber and predicts a final osmotic equilibrium pressure based on that rate of change. Both the actual pressure within the sealed solvent chamber and the calculated osmotic equilibrium pressure are recorded on an electrical recording device.

BRIEF DESCRIPTION OF THE DRAWINGS

The foregoing and other features and advantages of the invention will be apparent from the following more particular description of the preferred embodiment of the invention, as illustrated in the accompanying drawings, in which like reference characters refer to the same parts throughout the different views. The drawings are not necessarily to scale, emphasis instead being placed upon illustrating the principles of the invention.

PREFERRED EMBODIMENTS OF THE INVENTION

Figure 3:
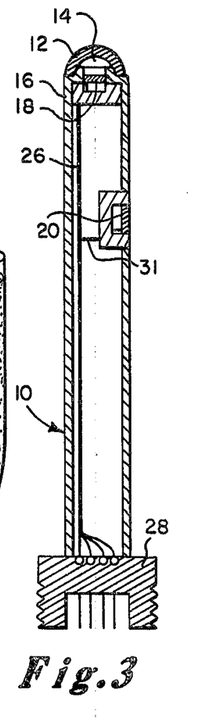
FIG. 3 is a cross-sectional view of a miniature osmometer for in vivo use.

FIG. 3 is a cutaway view of a miniature osmometer displaying a fully assembled sensor 10 for insertion into a patient. The osmometer is constructed both for easy insertion into a patient and durability. A hard, hemispherical, semipermeable membrane 12 is attached by screw or adhesive means to a pen-like capsule 16 of the osmometer 10. The membrane is a dome constructed of a rigid plastic ceramic. Assembly of the membrane 12 to the capsule 16 should preferably be done in a bath of degassed solvent. In this way bubbles are eliminated and possible cavitation in the solvent chamber 14 during use is prevented.

Across the membrane 12 there is a transfer of fluid from an inner chamber 14 and into a patient. The inner chamber 14 contains a pure solvent, which is physiological saline for in vivo usage. The hard semipermeable membrane dome 12 is equivalent to the semipermeable membranes previously discussed. The pure solvent inside the dome tends to flow outward and across the semipermeable membrane. This causes a decrease in pressure inside the inner chamber 14. This decrease in pressure continues until equilibrium is reached. At equilibrium the differential pressure inside and outside the semipermeable dome is equal to the colloid osmotic pressure. The change in pressure is sensed by the pressure sensor 18 bordering the chamber.

The pressure sensor 18 is of conventional construction as now available in the instrument market. Pressure sensors may currently be acquired at diameters smaller than one millimeter. The diameter of the osmometer barrel 16 would therefore be only slightly larger than that of the pressure sensor, i.e., one or two millimeters.

Below the first pressure sensor 18 is a lower sensor 20 equivalent in construction to pressure sensor 18. Pressure sensor 20 is positioned at the side of the capsule to measure the hydrostatic or ambient pressure of the fluid whose osmotic pressure is desired.

The in vivo hydrostatic or ambient pressure is used for calculating the osmotic pressure in the computer program described below. The hydrostatic pressure is the initial pressure on the fluid and must be subtracted from the observed pressure in the chamber 14. By relating these two pressures, variations in hydrostatic or ambient pressure may be eliminated as a factor in the osmotic equilibrium pressure measurement. The electrical leads from the first transducer 26 and the second transducer 31 are led from the sealed compartment through the barrel of the osmometer to the integral electrical connector 28. Alternately the capsule 16 may be implanted within the subject and pressure data recorded by means of a telemetry system.

Alternately the osmometer may be constructed to hydraulically subtract the ambient pressure by exposing the pressure sensor which borders the solvent chamber to ambient pressure on its reverse side.

Figure 4:
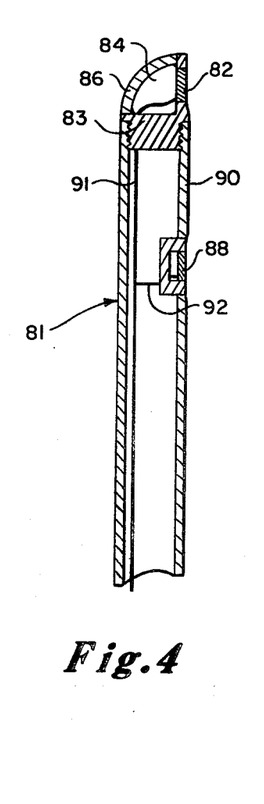
FIG. 4 is a cross section of a second embodiment of an in vivo osmometer.
Figure 5:
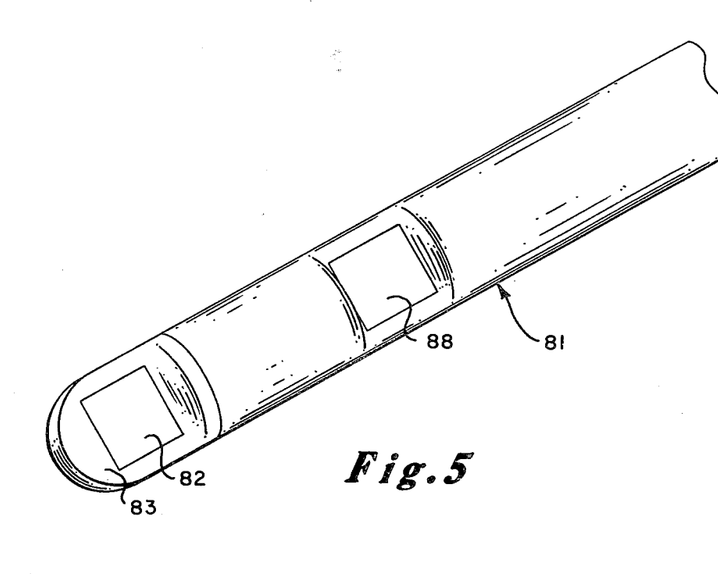
FIG. 5 is a perspective view of the second embodiment.

FIG. 4 is a cross section of a miniature osmometer 81 in which the ambient pressure is hydraulically subtracted from the solvent chamber pressure. FIG. 5 is a perspective view of this same osmometer.

Pressure sensor 82 in osmometer end cap 83 borders both the solvent chamber 84 and the external environment. Chamber 84 is filled with degassed solvent and communicates with the environment to be tested through hard semipermeable membrane 86. A separate sensor 88 may also be included on the barrel of the capsule to sense ambient or hydrostatic pressure if desired. Sensor leads 91 and 92 are led out to a connector as in the first embodiment of FIG. 3 unless telemetry is required.

Figure 6:
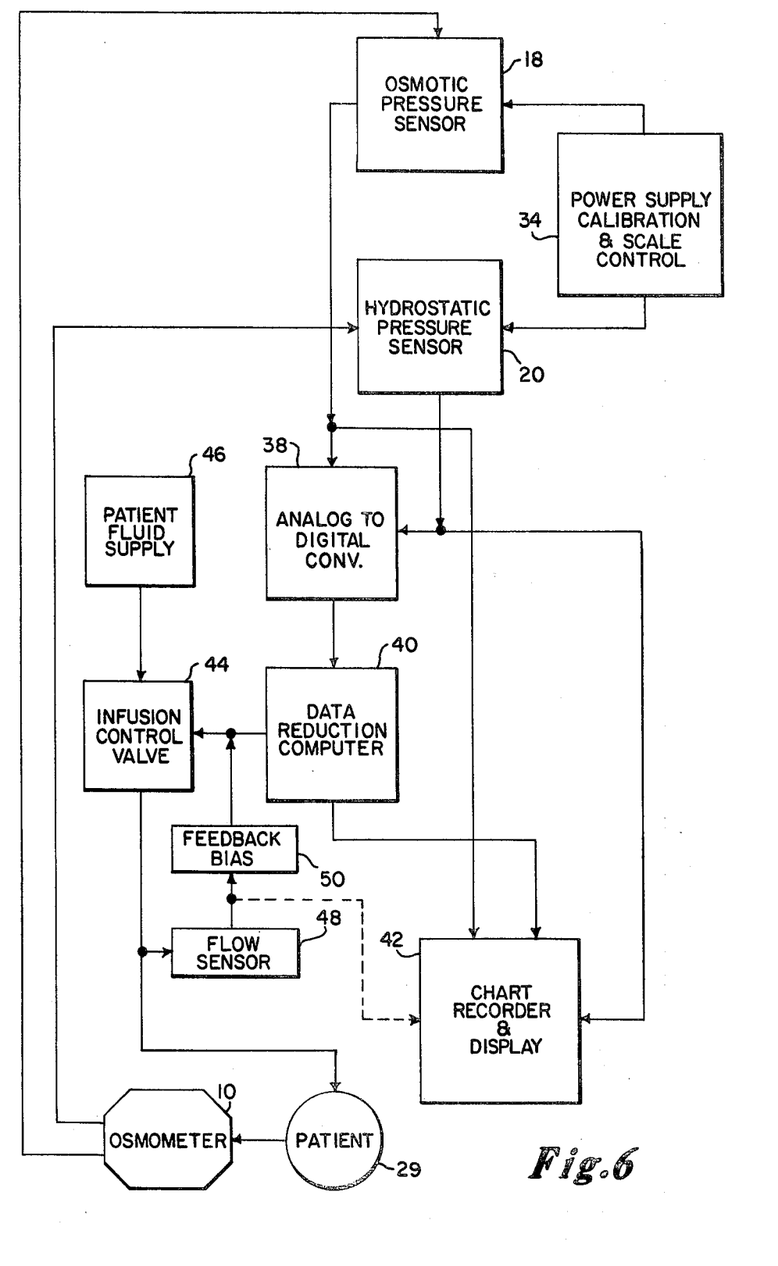
FIG. 6 is the flow diagram of a miniature osmometer and its associated computer control and readout apparatus which can be connected to a servo system that can control the rate of infusion of fluids into the vasculature of a patient.

FIG. 6 is a block diagram showing the complete measurement system composed of an in vivo osmeter with control and data analysis apparatus. When the osmometer 10 or 81 is inserted into the patient 29, signals corresponding to the pressure in the osmometer pressure chamber 14 and the in vivo hydrostatic pressure are generated by the osmometer pressure sensor 18 and the hydrostatic pressure sensor 20. The signals from the pressure sensors are fed directly both to a display and chart recorder 42 and to analog-digital converter 38. The pressure sensors 18, 20 both receive their power and send their signals through the integral connector 28 (FIG. 3). Through the power supply 34 adjustment of calibration and scale of the pressure sensors may be made.

The analog-digital converter 38 converts the modulated voltage signals of the pressure sensors 18, 20 to pulses forming digital code representations of the voltage signals. When it is necessary to correct for the hydrostatic pressures of the fluid in which the osmometer is immersed, the hydrostatic head pressure recorded from sensor 20 is electrically subtracted from the output from sensor 18. Once the analog signals are converted to digital signals, the data recording computer 40 uses the signals to generate a predicted osmotic equilibrium point by solving a first order differential equation. In this way, the data analysis system gives a final predicted value of equilibrium colloidal osmotic pressure from only a brief reading of the pressure-time development curve sensed by the probe rather than waiting five or more minutes for an empirical reading at equilibrium.

The rate of approach to equilibrium in the osmometer chamber 14 is a first order process, in that the rate of approach to equilibrium is proportional to the pressure differential across the semipermeable membrane. This can be stated mathematically as $$dp/dt = k(P - P_{eq}) \tag{1}$$

where P is the pressure in the osmometer under the dome 14 at any time, $P_{eq}$ is the equilibrium pressure under the dome, t is real time and k is a constant.

Below is the solution (2) for equilibrium pressure ($P_{eq}$) as predicted from a brief sensing of the pressure-time curve.

$$P_{eq} = \frac{2 \int_{t_o}^{t} P^2 dt - (P + P_o) \int_{t_o}^{t} P dt}{2 \int_{t_o}^{t} P dt - (P + P_o)(t - t_o)} \tag{2}$$

$P_o$ and $t_o$ are the initial conditions on the pressure-time curve. In essence the derivation (2) eliminates the constant k by solving two simultaneous differential equations using the least squares methodology. One of the equations is obtained by differentiation with respect to k. The other is obtained by differentiation with respect to $P_{eq}$. Once k is eliminated, $P_{eq}$ can be expressed as a series of summations of multiple discrete functions of measured pressure (P) and its rate of change over time.

These discrete functions can then be put into continuous form by letting the number of them approach a time continuum (n→t). To obtain $P_{eq}$ from a small temporal portion of the curve, the computer records initial conditions (Po, to) on the pressure-time curve and introduces the recorded pressure (P) and time (t). The computer's solution of equation (2) is recorded on the chart recorder 42 adjacent to the direct readings of the osmotic pressure in chamber 14 in real time. If possible, sensing may be continued until equilibrium is reached, at which time the two values $P_{eq}$, predicted and P in chamber 14 should be equal.

After the computer data reduction has been completed, the predicted equilibrium value is sent as a scaled voltage to a chart recorder 42 and to an infusion control valve 44. The infusion control valve controls the amount of fluid that the patient 29 receives from a fluid supply reservoir 46. This may be either saline solution or dialysis solution. In this way, a patient's osmotic pressure can be maintained at normal levels.

A flow sensor or metering device 48 measures the amount of fluid supply through the control valve. A feedback circuit is also included in the circuit from the data reduction computer to the control valve so as dampen fluctuations in valving. By this method, the infusion control valve is properly damped and does not subject the patient to sharp changes in a fluid transfusion. The measurement of the transfusion rate by the flow sensor may be read at the chart recorder display 42. This is shown by a dotted line.

The chart recorder 42 and display has at least one pen to record the pressure in chamber 14 directly from the osmotic pressure sensor 18 and the predicted equilibrium state which has been calculated by the data reduction computer 40. In addition, the chart record may display hydrostatic pressure from sensor 20 and the rate of transfusion of fluid into the patient as monitored by the flow sensor 48. In this way, the system can be monitored by medical personnel.

Figures 7, 7A:
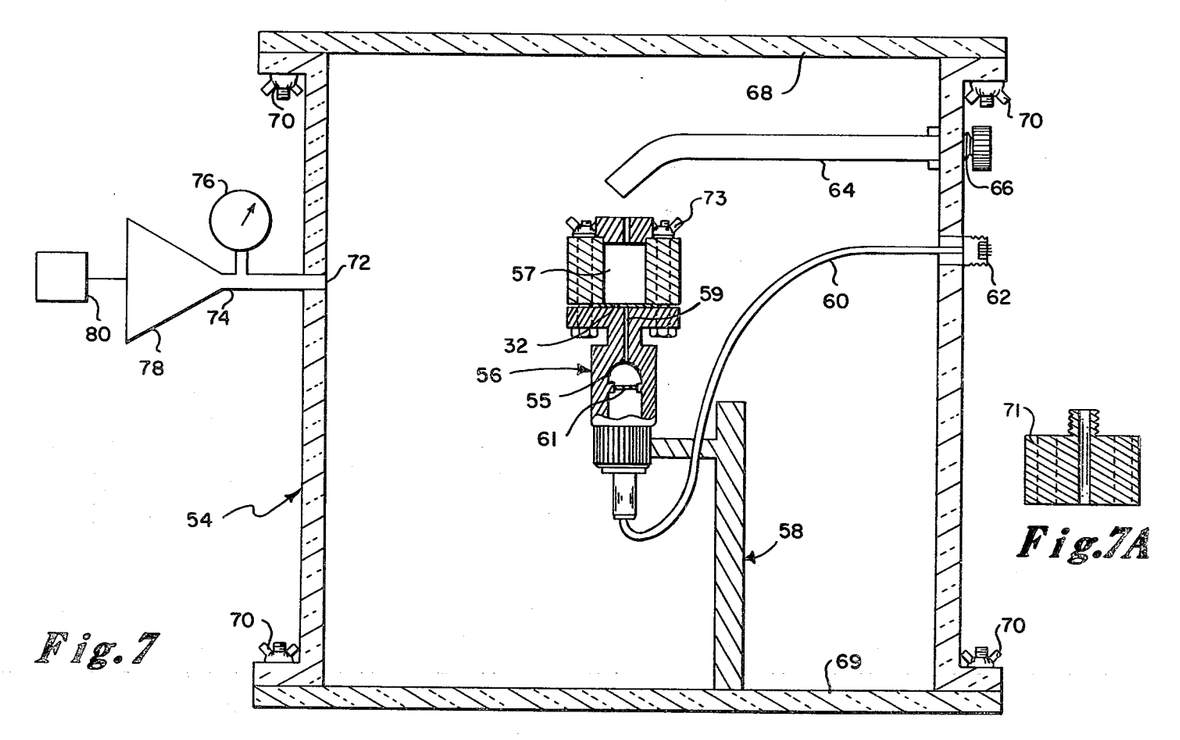
FIG. 7 is a cross sectional view of a high pressure osmometer apparatus.
FIG. 7a is a cross section of the osmometer calibration fitting.

FIG. 7, an alternate embodiment, is a cross-sectional view of an osmometer pressure chamber apparatus. The osmometer is of the type disclosed in my prior U.S. Pat. No. 3,063,288. The high pressure osmometer works on the same principles as discussed above. In this application, however, the osmometer is used to measure high colloidal osmotic pressures in very concentrated solutions where the equilibrium pressure is greater than 1 atmosphere. The osmometer must be pressurized in order for the pressure sensor to have sufficient scale to measure solvent chamber decreases in pressure of greater than 1 atmosphere. Alternately the behaviors of solutions under high pressure environments is also a field of interest in use of the instrument. With high pressure measurements the time required to establish osmotic equilibrium may be very long indeed, therefore in order for osmometer measurements to be useful, a data reduction computer system must be used to predict osmotic equilibrium.

FIG. 7 shows the physical layout of the high pressure osmometer. The pressure chamber 54 is structured with an osmometer 56 held inside by a brace 58. The osmometer 56 has a solvent chamber 55 situated below a test solution chamber 57 and connected through passage 59. The semipermeable membrane 32 is situated below the test solution chamber 57. A pressure diaphragm 61 senses the change in volume of solvent in the solvent chamber 55 and therefore its pressure change. As explained above, pressure changes as a result of passage of solvent across the semipermeable membrane 32. All the components of the osmometer are exposed to the pressure environment of the pressure chamber 54, except for the interior of the osmotic chamber 55 which develops the osmotic pressure.

The pressure chamber 54 has removable top and bottom lucite plates 68 and 69 to allow access to the osmometer 56. Sealing fastening means 70 are applied and screwed down to retain pressure. The osmometer itself is connected to its power supply and data acquisition system through an electrical cable 60 and connector 62. The connector 62 is sealed against the pressure chamber wall so as to prevent pressure leaks. Osmometer calibration is performed through pressure tight junction 66 (normally capped) and a manometer tube 64, which is attached to fitting 71 (FIG. 7A). Fitting 71 is installed instead of chamber 57 and membrane 32 during calibration.

Test chambers 57 and 55 are constructed of clear lucite and maintained in position by thumb screws 73. Membrane 32 and sensor 61 are installed with the chambers.

During an experiment, the pressure in the chamber 54 is held constant. The pressure is controlled through vent 72, where conduit 74 allows for compressed air from a compressor 78 to be introduced into the chamber. The conventional compressor 78 is driven by a motor 80. The pressure in the chamber is measured at gauge 76 mounted on conduit 74.

Figure 8:
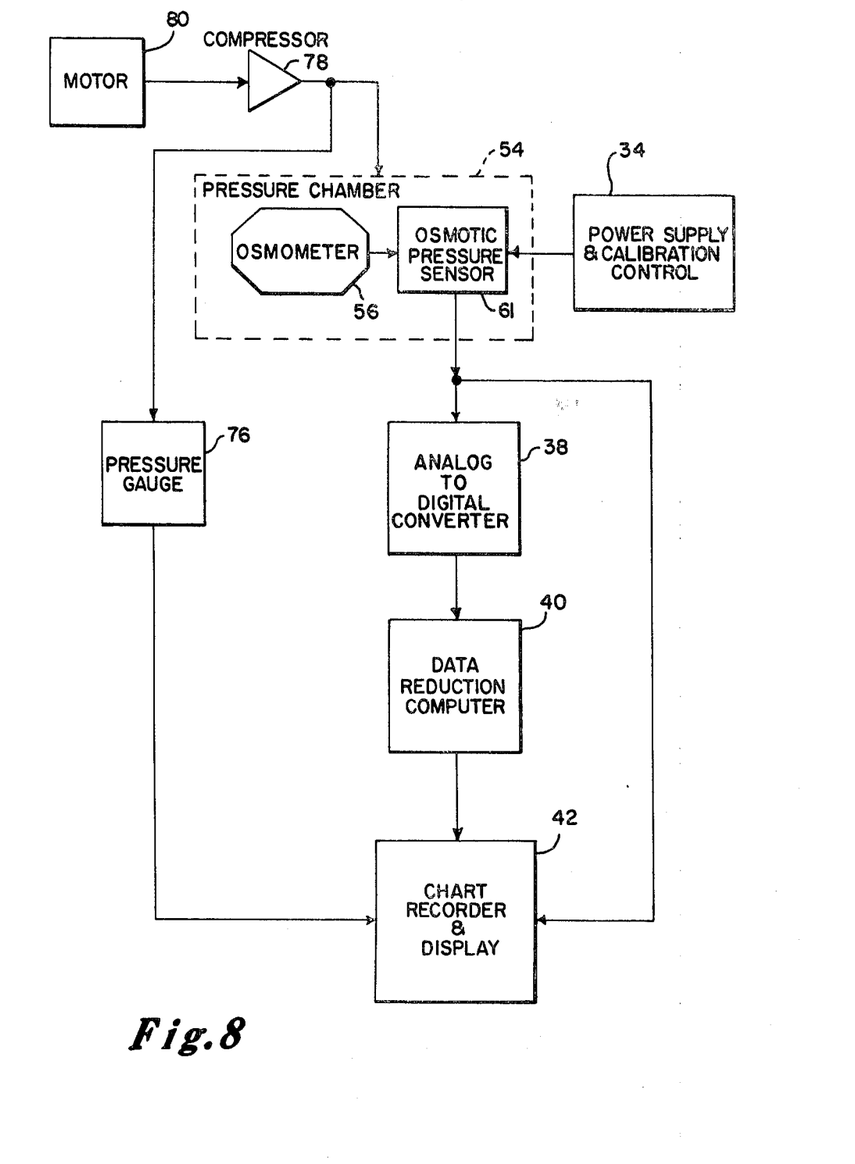
FIG. 8 is a flow diagram of a high pressure osmometer and its associated control and recording apparatus.

FIG. 8 shows the flow diagram of the osmometer system used for high pressure measurements. The signal from the osmometer pressure sensor 61 is fed both to the Analog-digital converter 38 and directly to the chart recorder and display 42. The Analog-digital converter and the data reduction computer 40 operate the same way as detailed in the prior embodiment shown in FIG. 6. From a small section of pressuretime measurement curve, the computer calculates a predicted equilibrium osmotic pressure which is displayed on the chart recorder and display 42.

The internal pressure of the chamber which is sensed at the pressure gauge 76 is also recorded and displayed at the chart recorder 42. The compressor 78 is used to pressurize the chamber to produce the high pressure environment. Since the test solution and back of the transducer diaphragm are maintained at equal pressure, no hydrostatic pressure correction is required. The osmometer is balanced and calibrated from a power supply calibration and scale control box 34.

A system with a data reduction program as described in the previous embodiment is as necessary for high pressure measurements as it is for in vivo measurements. When the colloid osmotic pressure is very high, more time is required for osmotic equilibrium to be reached. For a valid measurement to be taken, pressure and temperature must remain constant and the sample stable. In order to minimize the transient influences and the environmental changes, the shortest possible sensing period is required for accurate measurement. The shorter the period in which equilibrium can be reliably calculated, the more accurate the measurement is liable to be. Such a system as described is extremely useful for medical and physical chemical research.

While the invention has been particularly shown and described with reference to preferred embodiments thereof, it will be understood by those skilled in the art that various changes in form and detail may be made therein without departing from the spirit and scope of the invention as defined by the intended claims. For example, various different pressure sensors may be used or an analog computer could be substituted for the digital computer used here.

I claim:

1. A colloidal osmometer for rapid read-out of osmotic equilibrium pressure comprising:
    a. a capsule of about 2 mm or less in cross sectional dimension suitable for in vivo insertion;
    b. a cap of rigid ceramic which forms a semipermeable membrane at an end of the capsule;
    c. a solvent chamber fully enclosed in the capsule covered at least in part by the cap of rigid ceramic; and
    d. a pressure transducer in the capsule adjacent to the solvent chamber providing an electrical output indicative of the pressure in the solvent chamber.

2. The colloidal osmometer recited in claim 1 wherein a second pressure transducer in the capsule is used for measurement of ambient pressure in the vicinity of the semipermeable membrane.

3. The colloidal osmometer recited in claim 1 wherein the capsule is generally cylindrical and the capsule diameter is smaller than 2 mm.

4. The colloidal osmometer recited in claim 1 wherein the solvent chamber is filled with degassed solvent.

5. A colloidal osmometer that gives rapid read-out of osmotic equilibrium pressure comprising:
    a. a pen-like capsule;
    b. a cap of rigid ceramic which forms a semipermeable pressure dome;
    c. a solvent chamber covered at least in part by the cap of rigid ceramic;
    d. a pressure transducer adjacent to the solvent chamber providing a pressure output; and
    e. electronic computing means for calculating the pressure rate of change across the semipermeable membrane and projecting the osmotic equilibrium pressure from said pressure output;
    f. an electrical recording device used to record predicted equilibrium data from said electronic computing means.

6. A colloidal osmometer as claimed in claim 5 wherein the recording device is a chart recorder with at least one pen capable of recording both the input data from the osmometer and the calculated data from said electronic computing means.

7. An osmometer for rapid determination of osmotic equilibrium pressure of a solution of solute in solvent comprising:
    a. a solvent chamber;
    b. a pressure sensor providing an output proportional to a change in pressure within the solvent chamber caused by passage of fluid across a semipermeable membrane bounding the solvent chamber;
    c. electronic computing means for calculating the solution's osmotic equilibrium pressure from the pressure sensor output over a period of time shorter than that required for osmotic equilibrium to actually occur by generating a mathematical solution for osmotic equilibrium pressure, as defined as $$P_{eq} = \frac{2 \int_{t_o}^{t} P^2 dt - (P + P_o) \int_{t_o}^{t} P dt}{2 \int_{t_o}^{t} P dt - (P + P_o)(t - t_o)}$$

wherein:

$P_{eq}$ is osmotic equilibrium pressure,
t is real time,
$P_o$ is initial pressure,
$t_o$ is initial time and,
P is pressure measured by the pressure transducer at a finite time.

8. A method of determining the in vivo colloid osmotic pressure of living subjects comprising the steps of:
    a. inserting into a subject a capsule with a solvent chamber bordered by a semipermeable pressure dome;
    b. measuring any change in pressure in the solvent chamber with a pressure transducer;
    c. measuring the ambient pressure of the fluid in which the probe is immersed;
    d. transmitting a pressure signal from a pressure transducer at the solvent chamber to an input for a computing device;
    e. computing the rate of change of the pressure within the solvent chamber as changed by passage of fluid across the semipermeable membrane;
    f. predicting a theoretical osmotic equilibrium pressure based on said rate of change; and,
    g. recording the theoretical osmotic equilibrium pressure on a recording device.

9. A method of controlling intravascular colloid osmotic pressure of a system comprising the steps of:
    a. inserting into the system a probe with a solvent chamber bordered by a semipermeable pressure dome;
    b. measuring any change in pressure in the solvent chamber with a pressure transducer;
    c. measuring the ambient pressure of the fluid in which the osmometer is immersed;
    d. transmitting a pressure signal from the pressure transducer at the solvent chamber to an input for a computing device;
    e. computing the rate of change of the osmotic pressure within the solvent chamber as changed by passage of fluid across the semipermeable membrane;
    f. predicting a theoretical osmotic equilibrium pressure based on said rate of change;
    g. recording both the data from the first pressure transducer and the calculated prediction on a recording device; and,
    h. controlling at least one valve to meter the rate of fluid solution infusion to the system.

10. A method of determining the osmotic pressure of solutions of substances in high pressure environments comprising the steps of:
    a. inserting into a pressure chamber an osmometer with a solvent chamber, a semipermeable membrane and, a solution whose osmotic pressure is to be measured;
    b. controlling environmental pressure in the chamber in which the osmometer and sample are positioned;

c. recording the change in pressure in the osmometer solvent chamber;
d. transmitting a signal from a pressure transducer in the osmometer to an input for a computing device;
e. computing a time rate of change of the osmotic pressure within the solvent chamber as changed by the passage of fluid across the semipermeable membrane;
f. predicting a theoretical final osmotic equilibrium pressure based on the time rate of change of pressure within solvent chamber of osmotic pressure; and,
g. recording both actual osmometer pressure and the calculated osmotic equilibrium prediction on an electrical recording device.

11. A colloidal osmometer for in vivo measurement of osmotic equilibrium pressure comprising a transducer assembly of about 2 mm or less in cross sectional dimension suitable for in vivo insertion, the transducer assembly having a solvent chamber fully enclosed therein near the tip thereof closed by a semipermeable membrane which forms a part of an outer wall of the transducer assembly and a pressure transducer in the transducer assembly adjacent to the solvent chamber for providing an electrical output indicative of the pressure in the solvent chamber.

* * * * *